(12) United States Patent
Busson et al.

(10) Patent No.: US 6,534,087 B2
(45) Date of Patent: Mar. 18, 2003

(54) PROCESS FOR PREPARING A PHARMACEUTICAL COMPOSITION

(75) Inventors: Patrick Busson, Bad Krozingen (DE); Marco Schroeder, Schopfheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/891,069

(22) Filed: Jun. 25, 2001

(65) Prior Publication Data

US 2002/0018812 A1 Feb. 14, 2002

(30) Foreign Application Priority Data

Jun. 27, 2000 (EP) ............................................. 00113535

(51) Int. Cl.$^7$ ............................. A61K 9/20; A61K 9/22; A61K 9/28; A61K 9/24; A61K 31/70
(52) U.S. Cl. ..................... 424/464; 424/468; 424/441; 424/473; 514/25; 514/449
(58) Field of Search ................................ 424/464, 468, 424/441, 473; 514/25, 449

(56) References Cited

U.S. PATENT DOCUMENTS

| | | | |
|---|---|---|---|
| 4,598,089 A | | 7/1986 | Hadvary et al. |
| 5,478,571 A | * | 12/1995 | Gala et al. .................. 424/464 |
| 6,004,996 A | | 12/1999 | Shah et al. |
| 6,030,953 A | * | 2/2000 | Bailly et al. .................. 514/25 |
| 6,299,906 B1 | * | 10/2001 | Bausch et al. .............. 424/489 |

FOREIGN PATENT DOCUMENTS

| | | |
|---|---|---|
| EP | 0759917 | 3/1997 |
| EP | 0976734 | 2/2000 |
| WO | WO 94/27995 | 12/1994 |
| WO | WO 96/40077 | 12/1996 |
| WO | WO 98/02240 | 1/1998 |
| WO | WO 99/34786 | 7/1999 |
| WO | WO 00/09122 | 2/2000 |
| WO | WO 00/09123 | 2/2000 |
| WO | WO 00/40569 | 7/2000 |

OTHER PUBLICATIONS

Sinnamon et al, *J. Dairy Sci.*, 40, pp. 1036–1045 (1957).
Schroeder, Ph.D. thesis, "Entwicklung von kompakten Darreichungsforment aus spruhgetrockneten Milcherzeugnissen zur spontanen Rekonstitution" (1999).
Mutoh et al, *J. Antibiot*, 47(12), pp. 1369–1375 (1994).

* cited by examiner

*Primary Examiner*—Jose' G. Dees
*Assistant Examiner*—Robert M DeWitty
(74) *Attorney, Agent, or Firm*—George W. Johnston; John P. Parise

(57) ABSTRACT

A method for the preparation of compositions, preferably pharmaceutical compositions, in form of expanded, mechanically stable, lamellar, porous, sponge-like or foam structures out of solutions and dispersions results in a favored pharmaceutical product. This method comprises the steps of a) preparing a solution or a homogeneous dispersion of a liquid and a compound selected from the group consisting of one or more pharmaceutically active compounds, one or more pharmaceutically suitable excipients, and mixtures thereof, followed by b) the expansion of the solution or the homogeneous dispersion without boiling.

29 Claims, No Drawings

PROCESS FOR PREPARING A PHARMACEUTICAL COMPOSITION

BACKGROUND OF THE INVENTION

1. Field

The present invention relates to a method for preparing compositions, preferably pharmaceutical compositions, in form of expanded, mechanically stable, lamellar, porous, sponge-like or foam structures out of solutions and dispersions and to dosage forms obtainable by the above method.

2. Description

Pharmaceutical technology formulation work is mostly determined by physico-chemical properties of the pure active drug substance (particle size and shape, flowability, compressibility, polymorphism, wettability, melting point, stability, shelf-life etc.) or other important additives. Many dosage forms are known to the pharmaceutical market, the most important being tablets and capsules. The stabilization of highly sensitive drugs that are supposed to be used or applied orally or parenterally after rehydration, such as dry solutions or dispersions (e.g. suspensions, emulsions) are of major interest.

Downstreaming the pure drug substance into the final market formulation normally comprises several fundamental operations such as milling, seizing, wet or dry granulation, slugging, encapsulation etc. Today, many of these processes are designed to manufacture large amounts of material, e.g. high-speed tabletting. Mechanical energy, produced by impact, pressure or shear stress, can be detrimental to the material. Very often this leads to melting, decomposition or inactivation of the drug substance. Deposits or incrustations caused in this manner may interrupt the process or even destroy the machines.

To facilitate the manufacturing process of dosage form, drug substance has normally to be mixed, blended or granulated with different pharmaceutical excipients, such as lubricants, filler, binder, flowing or dispersing agents etc. These additives can influence the properties of the final composition but can only partially protect against mechanical energy and can even induce stability problems by themselves.

The final composition as well as the corresponding dosage form is also supposed to have very specific properties before, during or after application. For bulk materials (powders, granules, pellets, tablets etc.) high stability and compatibility are desired during storage. Dry suspensions must show exquisite dispersibility in liquids; tablets have to disintegrate either very fast or very slowly after being swallowed. A sufficient wettability of drug particles in gastric or intestinal fluids is a prerequisite for good solubility and absorption. As they are dosed by volume, pharmaceutical powders or granules need sufficient bulk density for tabletting or encapsulation. Depending on dose, these important galenical properties can be negatively impacted by a drug substance or excipient with unsuitable physico-chemical properties (e.g. low melting point; low solubility etc.).

In summary, manner in which a pharmaceutically active compound or pharmaceutically suitable excipient(s) is incorporated into a galenical composition or formulation can be a critical factor that has to be controlled. This manner is essential to:
mask undesirable properties;
stabilize, inertize and protect the critical, incorporated compound;
obtain optimal flowability and density for downstream work; and
get the necessary dispersibility and release characteristics during or after application.

Several techniques for improving these properties are known in the art. However, they very often are not able to overcome all problems and can even induce new problems. For example:
fluid bed coating is not suitable for substances having low melting points or fine and light particles having very high surface area and cylindrical or pin shape;
powders out of (co)precipitation processes (e.g. spray-drying) retain significant amounts of reactive material located to the particle surface;
freeze-drying is very expensive and not suitable for substances that are sensitive to freeze-thaw cycles; and
spray-congealing, melt-embedding or melt-extrusion are only feasible for temperature resistant materials.

International Patent Application WO 96/40077 (Quadrant Holdings Cambridge Limited) discloses a method for the preparation of thin, foamed glass matrices. This method comprising the steps of (a) preparing an initial mixture comprising at least one glass matrix-forming material and at least one solvent including a solvent for the glass matrix-forming material, (b) evaporating bulk solvent from the mixture to obtain a syrup, (c) exposing the syrup to a pressure and temperature sufficient to cause boiling of the syrup, and (d) optionally removing the residual moisture.

International Patent Application WO 98/02240 (Universal Preservation Technologies) discloses a method of preserving sensitive biological dispersions, suspensions, emulsions and solutions by forming stable foams from fluid materials to be dehydrated, as an aid both to the drying of one or more biologically active substrates in the fluid and as an aid in preparing an easily divisible dried product suitable for further commercial use. The stable foams are formed by partially removing the water to form a viscous liquid and by further subjecting the reduced liquid to vacuum, to cause it to boil during further drying at temperatures substantially lower than 100° C. In other words, reduced pressure is applied to viscous solutions or suspensions of biologically active materials to cause the solutions or suspensions to foam during boiling, and using the foaming process further solvent removal causes the ultimate production of a stable open-cell or closed-cell foam.

However, both references disclose boiling as necessary step to prepare compositions. In addition, the mixtures, solutions, emulsions or dispersions have initially to be concentrated by evaporating bulk solvent to obtain the necessary syrup for further use (low vacuum; <30/<24 Torr). Then, after having obtained a syrup of sufficient viscosity, "foaming" (expansion of structure) is carried out at temperature and pressure conditions that cause the syrup to boil.

Sinnamon et al. [*J. Dairy Sci.,* 40: 1036–1045 (1957)] discloses the properties of a new dry whole milk, dried under high vacuum and low temperatures in the form of an expanded sponge-like structure. The obtained product disperses easily in cold water and has a natural flavor when reconstituted in the fresh state. However, this method was devised to improve dispersibility and flavor of food products such as dried milk. As a disadvantageous prerequisite, an initial concentration step (up to 50% w/w solids) is necessary for the following foaming process, too. Only when nitrogen will be bubbled through said concentrated milk, the requested "puffed" foam structure is achievable.

Schroeder [Ph. D. thesis entitled "Entwicklung von kompakten Darreichungsformen aus sprühgetrockneten Milcherzeugnissen zur spontanen Rekonstitution" (1999)] discloses mainly the development of a technology which provides densification of dairy or non-dairy food products without changing the instant properties of the originally spray dried powders during reconstitution. However, the described method for vacuum drying of wetted powders took place under conditions (50° C./37.5 Torr) which caused the incorporated water to boil while the requested foam structure was created.

The long felt problem in the art is to provide a processes and compositions that minimize the mentioned disadvantages.

SUMMARY OF THE INVENTION

The subject invention provides a method for preparing a pharmaceutical composition. This method comprises (a) preparing a solution or a homogeneous dispersion, (b) expanding the solution or homogeneous dispersion by exposing it to a change in pressure under conditions such that the solution or homogeneous dispersion does not boil, and (c) stabilizing the expanded solution or homogeneous dispersion to form the pharmaceutical composition. In this method, the solution or a homogeneous dispersion contains a liquid and a compound selected from the group consisting of one or more pharmaceutically active compounds, one or more pharmaceutically suitable excipients, and mixtures thereof.

Stabilizing may occur inherently, but typically involves drying or cooling the composition. However, stabilizing does not require total dryness and the composition formed by this method can be a solid or a gel. The expanding of the solution or homogeneous dispersion generally comprises reducing the pressure, for example, between about 30 and about 150 Torr.

One favorable embodiment is where the compound is a pharmaceutically active compound, such as a lipase inhibitor, and in particular orlistat. Other favored embodiments are where the pharmaceutically active compound is oseltamivir or 5-[7-[2-(5-methyl-2-phenyl-oxazole-4-yl)-ethoxy]-benzothiophene-4-methyl]-2,4-thiazolidinedione or its sodium salt.

It is preferred for the solution or dispersion comprises an embedding material or glass matrix-forming material, especially a pharmaceutically suitable excipient. The embedding material or glass matrix-forming material can be a polyol, gum, polymer, or a pharmaceutically acceptable salt thereof. A favored polyol that is a carbohydrate, for example, maltodextrin, trehalose, cellobiose, glucose, fructose, maltulose, iso-maltulose, lactulose, maltose, gentobiose, lactose, isomaltose, maltitol, lactitol, erythritol, palatinitol, xylitol, mannitol, sorbitol, dulcitol and ribitol, trehalose, sucrose, raffinose, gentianose, planteose, verbascose, stachyose, melezitose, dextran, or inositol. Maltodextrin, maltitol, and trehalose are the more preferred carbohydrates. Another group of favored gums, polymers and pharmaceutically acceptable salts thereof are polyethylenglycol; modified or substituted starch; modified or substituted cellulose; povidone; polyvinyl-alcohol; acacia gum; carbomer; alginic acid; cyclodextrins; gelatin; guar gum; welan gum; gellan gum; tara gum; locust bean gum; fibers; carrageenan gum; glucomannan; polymethacrylates; propylene glycol alginate; shellac; sodium alginate; tragacanth; chitosan; and xanthan gum.

It has been found that the gum, polymer or pharmaceutically acceptable salts thereof can be a modified or substituted starch, such as pregelatinized starch, hydroxyethylstarch, and sodium starchoctenylsucciante. Also good is modified or substituted cellulose, for example methylcellulose, ethylcellulose, hydroxyethyl cellulose, hydroxypropyl cellulose, hydroxypropylmethyl cellulose, hydroxypropylmethyl cellulose phthalate, carboxymethylcellulose sodium, or cellulose acetate phthalate.

The solution or dispersion can also incorporate a tenside, for example anionic tensides, co-emulsifiers, cationic tensides, non-ionic tensides, and amphoteric tensides. Further examples include sodium lauryl sulfate, docusate sodium, caseinate sodium, salts of fatty acids, quaternary amines, cethylpyridiniumchloride, polyoxyethylene fatty acid esters, sucrose fatty acid esters, cetyl alcohol, fatty acid esters, cetostearyl alcohol, cholesterol, sorb itan fatty acid esters, polysorbats, poloxamers, tocopheryl polyethylene glycol succinate, and phospholipids.

The following are especially preferred solutions or dispersions: (i) about 5 to about 95% w/w water or a mixture of water/ethanol, about 1 to about 91% orlistat, about 3.9 to about 93.9% w/w maltodextrin, and about 0.1 to about 90.1% w/w of one or more pharmaceutically acceptable excipients; (ii) about 5 to about 95% w/w water or a mixture of water/ethanol, about 1 to about 91% orlistat, about 3.9 to about 93.9% w/w maltodextrin, and about 0.1 to about 90.1% w/w of polyoxyethylene fatty acid ester; (iii) aout 5 to about 95% w/w water or mixtures of water/ethanol, about 1 to about 91% w/w orlistat, about 1 to about 91% w/w trimyristin, about 2.9 to about 92.9% w/w maltodextrin, and about 0.1 to about 90.1% w/w polyoxyethylene fatty acid ester; (iv) about 3 to about 99.98% w/w isopropyl alcohol, about 0.01 to about 96.99% w/w oseltamivir, and about 0.01 to about 96.99% w/w polymethacrylate.

For all of the mentioned method variations, is preferred that the pharmaceutical composition has a residual solvent level between about 0.1 and about 10% w/w, a bulk (poured) density between about 0.1 and about 0.9 g/cm$^3$, and a particle size distribution between about 50 and about 600 μm.

Favored compositions include (i) a composition comprising about 0.2 to about 10% w/w residual water or a mixture of water/ethanol, about 1 to about 96% w/w orlistat, about 3.7 to about 98.7% maltodextrin, and about 0.1 to about 95.1% w/w of one or more pharmaceutically acceptable excipients and (ii) a composition which comprises from about 0.2 to about 10% w/w residual isopropyl alcohol, about 1 to about 98.8% w/w oseltamivir, and about 1 to about 98.8% w/w polymethacrylate.

DETAILED DESCRIPTION OF THE PREFERRED EMBODIMENTS

The invention will now be described in terms of its preferred embodiments. These embodiments are set forth to aid in understanding the subject invention but are not to be construed as limiting.

The subject invention provides a method for the preparation of a pharmaceutical composition comprising the steps of
a) preparing a solution or a homogeneous dispersion of a liquid and a compound selected from the group consisting of one or more pharmaceutically active compounds, one or more pharmaceutically suitable excipients, and mixtures thereof, followed by
b) expansion of the solution or homogeneous dispersion without boiling.

It was surprisingly found that the preparation of homogeneous, sufficient viscous solutions or dispersions prior to the expansion step is very feasible and creates several advantages compared to the techniques described as state of the art including no preliminary evaporation of bulk solvent necessary to obtain the right conditions for an expansion of the concentrate;

continuous process enabled for having a high throughput;

during expansion step requested supporting structure builds up at once (continuous process) or within a few minutes (batch process);

expansion takes place even under less critical pressure conditions (>30 Torr at ambient temperature), thus boiling of the concentrate is no initial prerequisite;

highly concentrated pharmaceutical compositions can be readily expanded and solidified within their capsule shell, blister pack etc. because of their low filling volume.

Examples of resulting benefits and possibilities with respect to physico-chemical and biopharmaceutical properties are protection and stabilization of pharmaceutically active compounds or pharmaceutically suitable excipients during processing and storage; expansion of shelf life; elimination of incompatibilities, independent from original properties desired physico-chemical characteristics can be generated according to the material used for embedding; the resulting morphology or the method of downstreaming (i.e. improved wettability, flowability, solubility etc.); taste-masking; reduction of side effects; higher bioavailability (especially for a pharmaceutically active compound solidified as amorphous glass) and/or control of release characteristics.

Unless otherwise indicated the following definitions are set forth to illustrate and define the meaning and scope of the various terms used to describe the invention herein.

The term "solution" as used herein means a physical system consisting of at least two compounds, wherein all compounds are molecularly distributed and come up as one phase.

The term "dispersion" means a physical system consisting of at least two phases. One of the phases is the dispersion medium, wherein one or more compounds (second or third phase) are uniformly distributed.

The term "pharmaceutically suitable" as used herein means that the substances used are acceptable from a toxicity viewpoint.

The term "boiling" refers to the vaporization of a liquid in case the pressure exerted by the surroundings upon a liquid is equaled by the pressure exerted by the vapor of the liquid; under this condition, addition of heat or reduction of pressure exerted by the surroundings results in the transformation of the liquid into its vapor without raising the temperature.

The term "glass-matrix forming material" refers to pharmaceutically active compounds or pharmaceutically suitable excipients, which appear in the amorphous state after solidification.

The term "embedding material" refers to substances that are able to coat, enclose, separate, protect or inertize other materials.

The term "expansion" means that the solution or homogeneous dispersion develops an increased volume and surface induced by a change in pressure and is thereby characterized by a coherent, lamellar, foam-, sponge- or cake-like structure.

The term "polyol" in connection with the present invention refers to a material out of the group of carbohydrates such as maltodextrin.

The term "gum" refers to a material that consists of a mixture of polysaccharides such as xanthan.

The term "polymer" refers to a material that is a macromolecule (natural or synthetic substance). It can be a homopolymer (i.e. polyethylenglycol) or a copolymer (i.e. polymethacrylate).

The term "lipase inhibitor" refers to compounds that are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat [Mutoh et al., *J. Antibiot.*, 47(12): 1369–1375 (1994)]. The term "lipase inhibitor" refers also to synthetic lipase inhibitors for example described in International Patent Application WO99/34786 (Geltex Pharmaceuticals Inc.). These polymers are characterized in that they have been substituted with one or more groups that inhibit lipases. The term "lipase inhibitor" also includes pharmaceutically acceptable salts of these compounds. The term "lipase inhibitor" also refers to 2-oxy-4H-3,1-benzoxazin-4-ones which have been described in International Patent Application WO00/40569 (Alizyme Therapeutics Ltd.), e.g. 2-decyloxy-6-methyl-4H-3,1-benzooxazin-4-one, 6-methyl-2-tetradecyloxy-4H-3,1-benzoxazin-4-one, and 2-hexadecyloxy-6-methyl-4H-3,1-benzoxazin-4-one. Most preferably, the term "lipase inhibitor" refers to orlistat.

The resulting pharmaceutical composition is a solid or gel-like composition, preferably a solid composition.

Optionally, the method is followed by drying and/or cooling the composition. This method is especially useful for preparing pharmaceutical compositions.

Preferably, the solution or homogeneous dispersion is expanded by decreasing pressure.

In a preferred embodiment, the solution or homogeneous dispersion is prepared by a liquid and a pharmaceutically active compound or pharmaceutically suitable excipient.

Preferably, the solution or dispersion is prepared by adding both a pharmaceutically active substance and a pharmaceutically suitable excipient to the liquid.

The liquid used in the above method should be easy to evaporate or vaporizable and may be selected from the group consisting of water (i.e. purified, deionized, distilled or sterilized water), aqueous buffer solutions or isotonics (i.e. hydrogen carbonate buffer pH 7.38), a nutrient medium or culture broth (i.e. peptone bouillon), alcohols (i.e. ethanol or isopropyl alcohol), ketones (i.e. acetone), ethers (i.e. diethyl ether), liquid hydrocarbons (i.e. octane), oils (i.e. essential oils such as camomile oil) and synthetics (i.e. plasma expander such as dextranes) but may not be limited to these. Also mixtures of the liquids mentioned above may be useful for the method of the present invention. Preferably, the liquid is an aqueous buffer and/or an isotonic solution.

The homogeneous dispersion may have the form of a colloid, sol, gel, liquid crystal, emulsion, paste, suspension or an ointment.

The solutions or homogeneous dispersions may be prepared by pouring the liquid or mixture of liquids into a planetary (or comparable) mixer, followed by dissolving and/or dispersing the pharmaceutically active compound(s) or pharmaceutically suitable excipient(s) in the liquid or mixture of liquids until said homogeneous dispersion is prepared. While mixing with the liquid or mixture of liquids the material(s) can be in the dry state, dissolved, dispersed or melted. Thereby or afterwards further compounds, excipients or liquids may be added.

In alternative, the solution s or homogeneous dispersions may be prepared by putting the pharmaceutically active compounds), pharmaceutically suitable excipient(s) or a mixture thereof into a planetary (or comparable) mixer, followed by wetting, dissolving and/or dispersing the material(s) with the solvent or mixture of solvents until said solution or homogeneous dispersion is prepared. Thereby or afterwards further compounds, excipients or liquids may be added.

In order to improve the homogeneity of the solution or dispersion, especially when the solid content is very high, the mixing or dispersing process may be supported by the use of i.e. a static mixer, microfluidizer, homogenizer, kneading devices, high shear forces, ultrasound, an ointment mill or other devices known by the art. The viscosity of the homogeneous solution or dispersion can be either low or high, provided that the mass remains feedable or spreadable.

The solution or dispersion is transformed into an expanded structure by exposing it to a change in pressure, as by vacuum or by puffing and is dried thereby or by contact, convection, radiation, sonification, high frequency, dry (hot or cold) gas or with the help of some desiccants like organic solvents, silica gel etc. In more detail, the homogenized solution or dispersion is normally pumped, distributed, spread or put either on a plate, sieve, belt, roll etc. or in a capsule shell, blister pack, vial, jar, syringe or other suitable form. Then, almost immediately (continuous process) or after a short time (batch process) a controlled change in pressure leads to the expanded structure. Thereby low pressure conditions between 30 and 150 Torr are suitable to provide excellent density of the resulting, solidified material.

According to the used liquid or mixture of liquids and the chosen temperature, expansion may be carried out by adjusting pressure conditions in a way that the homogenized solution or dispersion shall not boil. Dependent on the used composition, simultaneously or after stabilization of the expanded structure, pressure conditions may be varied, temperature may be changed or each drying method known by the art may be applied to get the desired residual solvent level. Drying can be an internal or external process and may be supported by vibration, fluidization or any other kind of well known technique that helps removing the fluid, solvent or the saturated gas phase. The above described variation of temperature and/or pressure conditions may be carried out in several steps (batch process) or in different zones (continuous process) wherein a final cooling step may be included.

For getting the desired shape, density and stability of the expanded structure, boiling of the liquid has to be avoided. The dried and optionally cooled structure expires a long shelf life and can easily be cut, crushed, milled respectively pulverized into a free flowing powder that on the one hand provides easy downstream processing like e.g. wet or dry agglomeration, (melt-) granulation, slugging, tabletting, compaction, pelletization, encapsulation or any other kind of filling process and on the other hand has excellent reconstitution properties in cold or tempered liquids or body fluids whereby the properties and efficacy of any embedded pharmaceutically active compounds or pharmaceutically suitable excipients are maintained. The described new method for preparing pharmaceutical compositions furthermore provides the possibility to create the expanded, sufficient dense structure directly in its final formulation or packaging ready for use.

The initial process for creating and drying said expanded structure can be batchwise (e.g. in a vacuum drying oven) or continuously (e.g. on a vacuum drying belt) or with the help of other techniques known by the art.

In a preferred embodiment, the compound of step a) is a pharmaceutically active compound. In another preferred embodiment, the compound of step a) is a pharmaceutically suitable excipient.

More specifically, the present invention refers to a method of preparing a pharmaceutical composition comprising the steps of
a) preparing a homogeneous solution or dispersion by mixing a pharmaceutically active compound and/or a pharmaceutically suitable excipient with a liquid or a mixture of liquids in a sufficient amount to create a homogeneous dispersion,
b) exposing the dispersion to a change in pressure without boiling, and
c) optionally drying and/or cooling the composition.

The above methods may also comprise the steps of a) preparing a solution or homogeneous dispersion by mixing a pharmaceutically active compound and a liquid or a mixture of liquids in a sufficient amount to create a solution or homogeneous dispersion, b) exposing the solution or dispersion to a change in pressure without boiling, and c) optionally drying and/or cooling the composition.

The above-described process is especially useful for the preparation of pharmaceutical compositions. Suitable pharmaceutically active compounds for this process may not be limited to any special group. The above described method for preparing pharmaceutical compositions is basically supposed to be a powerful tool whenever physico-chemical, technical, galenical or biopharmaceutical problems occur during or after development of pharmaceutically relevant products (i.e. drugs, medicaments, vitamins, medical devices). Nevertheless lipase inhibitors are especially preferred compounds to be used in the above process, preferably orlistat.

Orlistat, a gastrointestinal lipase inhibitor, also known as orlistat, is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123.

Other examples for pharmaceutically active compounds are neuraminidase inhibitors, e.g. oseltamivir and insulin sensitizers, e.g. 5-[7-[2-(5-methyl-2-phenyl-oxazole-4-yl)-ethoxy]-benzothiophene-4-methyl]-2,4-thiazolidinedione or its sodium salt. These compounds are known in the art and are described for example in European Patent Applications Nos. 96912404.9 and 99117934.2, and International Patent Application WO 94/27995, respectively.

In a preferred embodiment of the present invention the above solutions or dispersions further comprise an embedding or glass matrix-forming material. Preferably, the embedding or glass matrix-forming material is a polyol, gum, polymer, or pharmaceutically acceptable salts thereof.

The embedding or glass matrix-forming material may be the pharmaceutically active compound, highly dispersed as crystalline respectively solidified in the amorphous state or the pharmaceutically suitable excipient, preferably a polyol, e.g. a carbohydrate. The embedding or glass matrix-forming material may be amorphous, partly or fully crystalline.

The carbohydrate as pharmaceutically suitable excipient may be selected from the group consisting of maltodextrin, trehalose, cellobiose, glucose, fructose, maltulose, isomaltulose, lactulose, maltose, gentobiose, lactose, isomaltose, maltitol, lactitol, erythritol, palatinitol, xylitol, mannitol, sorbitol, dulcitol and ribitol, sucrose, raffinose, gentianose, planteose, verbascose, stachyose, melezitose, dextran and further inositol but may not be limited to these. In a preferred embodiment, the carbohydrate is maltodextrin. In a further preferred embodiment, the carbohydrate is trehalose. In another preferred embodiment, the carbohydrate is maltitol. The term "maltodextrin" preferably refers e.g. to Glucidex Roquette, the term "trehalose" preferably refers e.g. to Trehalose Merck, and the term maltitol preferably refers e.g. to Maltisorb Roquette.

Other pharmaceutically suitable excipients for use may be selected from the group of polymers, gums and their salts such as polyethylenglycol; modified or substituted starch (e.g. pregelatinized starch, hydroxyethylstarch, sodium starchoctenylsuccinate, inulin etc.); modified or substituted cellulose (e.g. methylcellulose, ethylcellulose, hydroxyethyl cellulose, hydroxypropyl cellulose, hydroxypropylmethyl cellulose, hydroxypropylmethyl cellulose phthalate, carboxymethylcellulose sodium, cellulose acetate phthalate etc.); povidone; polyvinyl-alcohol; acacia gum; carbomer; alginic acid; cyclodextrins; gelatin; guar gum; welan gum; gellan gum; tara gum; locust bean gum; fibers (i.e. pectin); carrageenan gum; glucomannan; polymethacrylates; propylene glycol alginate; shellac; sodium alginate; tragacanth xanthan gum; and chitosan but may not be limited to these.

Some of the mentioned materials may be fully amorphous or can also appear partially or fully in the crystalline state.

The above-described process is also useful for the preparation of pharmaceutical compositions wherein a pharmaceutically suitable excipient is prepared according to the above described processes. Any pharmaceutically suitable excipient for this kind of process can generally be selected from all possible groups of adjuvants that help transform the pharmaceutically active compound into its final formulation, modify or optimize its efficacy, change its properties, immobilize its molecules or preserve its stability. The invention is appropriate to improve desirable properties of an inert pharmaceutically suitable excipient as well as to mask properties undesirable. Some of the preferred groups of pharmaceutically suitable excipients comprise compounds selected from solvents, solubiliser, dissolution enhancer, salt forming agents, (volatile) salts, buffers, effervescent agents, stabilizing agents, gel former, tensides, lipids, fatty acids, antioxidants, synergists, chelating agents, preservatives, filler, bulking agents, carrier, adsorbents, binder, disintegrants, glidants, lubricants, separating agents, flow promoter, coating agents, retarding agents, coloring agents, pigments, odor and taste adjusting/-masking agents, resorption enhancer, moisture adjusting agents, flocculating agents etc.

Particularly, the invention refers to the above methods, wherein the pharmaceutically active compound is selected from the group consisting of e.g. molecules, drugs, vitamins, minerals, trace elements, enzymes, cells, sera, vaccines, proteins, viruses, bacteria, nucleic acids, complexes, liposomes or nanoparticles but may not be limited to these.

Especially, the present invention refers to methods, wherein the solution or dispersion comprises a tenside. Tensides in the sense of the present invention refer to pharmaceutically suitable excipients with emulsifying, stabilizing, solubilizing, wetting, anti-foaming or spreading properties. These adjuvants have an amphiphilic character and influence the interfacial tension between different phases. The term "tensides" comprises anionic tensides or co-emulsifier (i.e. detergents, sulfonates, sodium lauryl sulfate, docusate sodium, caseinate sodium, salts of fatty acids), cationic tensides (i.e. quaternary amines, cethylpyridiniumchloride), non-ionic tensides (i.e. polyoxyethylen fatty acid esters, e.g. polyoxyl 40 stearate, sucrose fatty acid esters, cetyl alcohol, fatty acid esters, cetostearyl alcohol, cholesterol, sorbitan fatty acid esters, polysorbats, poloxamer, tocopheryl polyethylene glycol succinate) and amphoteric tensides (i.e. phospholipids, ampholyts, proteins). In a preferred embodiment, the tenside is a polyoxyethylene fatty acid ester. In a further preferred embodiment, the tenside is a phospholipid. Preferably, the tenside selected from the group consisting of sodium lauryl sulfate, docusate sodium, caseinate sodium, salts of fatty acids, quaternary amines, cethylpyridiniumchloride, polyoxyethylene fatty acid esters, sucrose fatty acid esters, cetyl alcohol, fatty acid esters, cetostearyl alcohol, cholesterol, sorbitan fatty acid esters, polysorbats, poloxamers, tocopheryl polyethylene glycol succinate, and phospholipids.

More specifically, the above-described method refers to solutions and dispersions comprising from 3 to 99.99% w/w solvent(s) and 0.01 to 97% w/w pharmaceutically active compound(s) or 0.01 to 97% w/w pharmaceutically suitable excipient(s). The invention also refers to a method as described above, wherein the solution or dispersion comprises from 3 to 99.98% w/w solvent(s), 0.01 to 96.99% w/w pharmaceutically active compound(s), and 0.01 to 96.99% w/w pharmaceutically suitable excipient(s). Further, the above described solutions or dispersions may comprise from 3 to 99.98% w/w solvent, 0.01 to 96.99% w/w pharmaceutically active compound, and 0.01 to 96.99% w/w of a polyol. More preferably, the above described solutions or dispersions may be prepared from 3 to 99.97% w/w solvent, 0.01 to 96.98% w/w pharmaceutically active compound, 0.01 to 96.98% w/w polyol and 0.01 to 96.98% w/w of a tenside. Further, the invention refers to the above methods, wherein the dispersion comprises the solution or dispersion comprises from 3 to 99.98% w/w solvent, 0.01 to 96.99% w/w pharmaceutically suitable excipient and 0.01 to 96.99% w/w of a polyol, and to methods, wherein the solution or dispersion comprises from 3 to 99.98% w/w water or mixtures of water/ethanol, 0.01 to 96.99% w/w phospholipid and 0.01 to 96.99% w/w maltodextrin. The invention also refers to the above methods, wherein the solution or dispersion comprises from 3 to 99.98% w/w solvent, 0.01 to 96.99% w/w pharmaceutically active compound and 0.01 to 96.99% w/w of a pharmaceutically suitable excipient. In addition, the invention relates to the above methods, wherein the solution or dispersion comprises from 5 to 95% w/w water or a mixture of water/ethanol, 1 to 91% orlistat, 3.9 to 93.9% maltodextrin and 0.1 to 90.1% w/w of one or more pharmaceutically acceptable excipients as decried above. An especially preferred embodiment of the present invention refers to a method wherein the solution or dispersion is made from of 5 to 95% w/w solvent, preferably water or mixtures of water/ethanol, 1 to 91% w/w orlistat, 3.9 to 93.9% w/w maltodextrin and 0.1 to 90.1% w/w of polyoxyethylene fatty acid ester. A further preferred embodiment of the present invention refers to the above methods wherein the solution or dispersion comprises from 5 to 95% w/w water or mixtures of water/ethanol, 1 to 91% w/w orlistat, 1 to 91% w/w lipids, preferably trirhyristin, 2.9 to 92.9% w/w maltodextrin and 0.1 to 90.1% w/w polyoxyethylene fatty acid ester. Further, the invention relates to the above methods, wherein the solution or dispersion comprises from 3 to 99.98% w/w isopropylalcohol, 0.01 to 96.99% w/w oseltamivir, and 0.01 to 96.99% w/w polymethacrylate.

Particularly, the above method refers to the preparation of compositions, the solution or dispersion is prepared by pouring the solvent or mixture of solvents into a mixer, e.g. a planetary mixer or another suitable mixing devices known by the art, optionally adding a tenside or other suitable excipients and distributing them in the solvent or mixture of solvents. After dispersing the pharmaceutically active compound(s) or pharmaceutically suitable excipient(s) homogeneously within the fluid, the final solution or dispersion develops by optionally adding the polyol or other suitable excipients stepwise and by stirring, mixing, scraping or kneading continuously. Dependent on viscosity particle desagglomeration may be optimized by using e.g. a homogenizer or an ointment mill. Intrinsic particle size maybe controlled by laser diffraction or with a "grindometer" (metal block with a graduated groove and a scraper). The sequence of processing steps is variable and can be changed, if appropriate. The viscosity of the solutions or dispersions may be increased or decreased by adding one or more pharmaceutically suitable excipients.

In a preferred embodiment of the present invention, the expansion may be carried out within a temperature range of 20 to 35° C. and a reduction of pressure from 30 to 150 Torr, more preferably from 30 to 45 Torr. This may be performed by spreading the solution or homogeneous dispersion on plates or more preferably on sieves, screens or nets and putting them into a vacuum drying oven (or another suitable device known by the art) which is tempered in the range from 20 to 35° C. With regard to the chosen temperature, reduction of pressure in the range from 30 to 150 or more preferably from 30 to 45 Torr creates the desired dense, expanded structure without boiling. Of course, dependent on the used solvent or mixture of solvents, temperature and pressure conditions may be varied, presupposed that the evaporated liquid does not boil during the expansion step. According to the present invention, parallel to or after solidification of the expanded structure an optional drying and/or cooling step may be carried out by varying temperature and/or pressure conditions.

A drying process may be an internal or external process and the drying temperature may be higher or lower than the expansion temperature. The drying pressure may be higher or lower than the expansion pressure. The drying may be supported by vacuum, heating, sublimation, vibration, fluidization, radiation, contact, convection, sonification, high frequency, dry (hot or cold) gas or with the help of some desiccants (i.e. organic solvents, silica gel etc.) or any other kind of well known technique that helps removing the fluid, solvent or the saturated gas phase. According to the present invention, after expansion and optional drying of the structure an additional cooling step may be applied. The cooling temperature may be higher or lower than 0° C. and lower than the drying temperature. The cooling process may be an internal or external process. Of course, the expansion, optional drying and/or cooling of the structure is carried out in several steps (batch process) or in different zones (continuous process). A continuous process may be carried out with a vacuum drying belt, a vacuum drying roll or other suitable devices known by the art.

The present invention refers also to the compositions obtainable by the above methods.

The compositions obtainable according to the present invention may be characterized by assay, volume, density (preferably bulk density of the crushed material), particle size distribution, surface measurement, relative humidity, residual solvent level, solid matter content, wettability, solubility, stability, disintegration time, release characteristics, X-ray diffraction, dynamic vapor sorption, microcalorimetry, thermogravimetry, differential scanning calorimetry etc. Preferably the expanded, readily dried and crushed compositions obtainable by the present invention are characterized by a residual solvent level between 0.1 and 99.9%, more preferably between 1 and 10% and most preferably between 2 and 5% w/w. The bulk (poured) density is between 0.1 and 0.9, more preferably between 0.2 and 0.8 and most preferably between 0.3 and 0.6 g/cm$^3$. The particle size distribution of these compositions, expressed as "d' (63.2%) value", may be between 50 and 600 $\mu$m, more preferably between 200 and 400 $\mu$m.

Especially, the present invention refers to a pharmaceutical composition, comprising 0.2 to 10% w/w residual water or mixtures of water/ethanol, 1 to 96% w/w orlistat, 3.7 to 98.7% w/w maltodextrin or maltitol and 0.1 to 95.1% w/w of one or more pharmaceutically acceptable excipients as described above, e.g. a polyoxyethylene fatty acid ester. Further, the present invention relates to a pharmaceutical composition comprising from 0.2 to 10% w/w residual isopropyl alcohol, 1 to 98.8% w/w oseltamivir, and 1 to 98.8% w/w polymethacrylate.

The above compositions are characterized by a residual solvent level between 0.1 and 99.9% w/w, more preferably between 0.2 and 10% w/w and most preferably between 1 and 5% w/w w/w. The bulk (poured) density is between 0.1 and 0.9, more preferably between 0.2 and 0.8 and most preferably between 0.3 and 0.6 g/cm$^3$. The particle size distribution of these compositions may be expressed as "d' (63.2%) value" between 50 and 600 $\mu$m, more preferably between 200 and 400 $\mu$m.

The compositions obtainable according to the above methods may be blown, cut crushed, sieved, milled, chopped, comminuted or shredded into a (free flowing) powder. The powder may be mixed, combined, blended, granulated, tableted or processed with one or more pharmaceutically active compounds or pharmaceutically suitable excipients. The compositions may be processed into a dust, aerosol, powder, granule, pellet, tablet, dragee, capsule, dry solution, dry syrup, dry emulsion, dry suspension or others known by the art.

The compositions obtainable according to the invention may be directly prepared in their final formulation and dosage form, respectively and more preferably directly in its packaging. The dosage form may be selected form the group consisting of a xerogel, tablet or capsule but may not be limited to these. The dosage form may also be directly prepared in its packaging. The packaging may be selected from the group consisting of a blister pack, vial, jar, sachet or syringe but may not be limited to these. The final product corresponding to the methods of the present invention may be a drug, medicament, vitamin, instant drink or medical device but may not be limited to these.

Orlistat is preferably orally administered from 60 to 720 mg per day in divided doses two to three times per day. Preferred is wherein from 120 to 360 mg, most preferably 120 to 180 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of functional dyspepsia and has obtained a body mass index of 25 or greater.

Further, the invention refers to the use of the below-defined compositions for the preparation of drugs, medicaments, vitamins, medical devices etc. useful for treatment and prevention of diseases as mentioned above.

The invention will be now illustrated in details by the following examples.

EXAMPLES

Example 1

Dispersion

This example describes a composition according to the invention including orlistat as pharmaceutically active compound. The amount of solvent necessary for preparing the homogeneous dispersion is expressed as percentage of dry mass (w/w). The original solvent content of the raw materials was not taken into consideration. This composition was used to improve flowability, wettability, dispersibility, efficacy and stability of the pharmaceutically active compound. In addition, an easy downstream processing into a powder respectively into capsules or tablets (by reducing the amount of maltodextrin to 80% and blending the resulting powder with 3% of polyethylenglycol) is enabled:

| | |
|---|---|
| Orlistat | 10.0% w/w |
| Trimyristin | 5.0% w/w |
| Polyoxyl 40 stearate | 2.0% w/w |
| Maltodextrin | 83.0% w/w |
| Water | 22.5% w/w |

Expansion

With the help of a syringe 100 g of homogeneous dispersion were spread on a sieve (mesh size 0.5 mm) in tracks. The sieve was put into a vacuum drying oven (Heraeus VT 5050 EK) which was tempered to 25° C. Chamber pressure was lowered to 30 Torr (Leybold Heraeus TRIVAC D8B; COMAT AG DPI 700). After 5 minutes, expansion of structure was completed.

Drying

By measuring mass and chamber temperature (AOiP PJN 5210) these conditions were fixed for about 30 minutes. Then, by keeping the same pressure conditions, chamber temperature was elevated to 50° C. The process was stopped after altogether 90 minutes, when the mass temperature reached the desired limit of 35° C. The residual solvent content can be adjusted according to the necessary amount for further processing.

Example 2

Dispersion

This example describes a composition according to the invention including oseltamivir as pharmaceutically active compound. The amount of solvent necessary for preparing the homogeneous dispersion is expressed as percentage of dry mass (w/w). The original solvent content of the raw materials was not taken into consideration. This composition was used to perform a taste-masking, to improve stability and shelflife, to reduce side effects and to prevent incompatibilities:

| | |
|---|---|
| Oseltamivir | 10.0% w/w |
| Polymethacrylate | 90.0% w/w |
| Isopropyl alcohol | 80.0% w/w |

Expansion 100 g of homogeneous dispersion were spread on a plate in tracks. The plate was put into a vacuum drying oven (Heraeus VT 5050 EK). At ambient temperature chamber pressure was lowered to 45 Torr (Leybold Heraeus TRIVAC D8B; COMAT AG DPI 700). After 5 minutes, expansion of structure was completed.

Drying

By keeping the same temperature and pressure conditions the expanded structure was dried over altogether 180 minutes.

Example 3

Dispersion

This example describes a composition according to the invention including phospholipid as pharmaceutically suitable excipient. The amount of solvent necessary for preparing the homogeneous dispersion is expressed as percentage of dry mass (w/w). The original solvent content of the raw materials was not taken into consideration. This composition was used to prevent stability problems and incompatibilities:

| | |
|---|---|
| Lecithin | 30.0% w/w |
| Maltodextrin | 70.0% w/w |
| Water | 40.0% w/w |

Expansion 100 g of homogeneous dispersion were spread on a sieve (mesh size 0.5 mm) in tracks. The sieve was put into a vacuum drying oven (Heraeus VT 5050 EK). At ambient temperature chamber pressure was lowered to 30 Torr (Leybold Heraeus TRIVAC D8B; COMAT AG DPI 700). After 5 minutes, expansion of structure was completed.

Drying

By measuring mass and chamber temperature (AOiP PJN 5210) these conditions were fixed for about 30 minutes. Then, by keeping the same pressure conditions, chamber temperature was elevated to 35° C. The process was stopped after altogether 120 minutes.

Example 4

Directly Prepared Dosage Form

Dispersion

This example describes a placebo composition respectively the direct preparation of its final dosage form according to the invention including maltodextrin and hydroxypropylmethyl cellulose as pharmaceutically suitable excipients. The amount of solvent necessary for preparing the homogeneous dispersion is expressed as percentage of dry mass (w/w). The original solvent content of the raw materials was not taken into consideration. This composition was used to demonstrate manufacturability, stability and weight uniformity of the directly prepared dosage forms in a blister pack:

| | |
|---|---|
| Maltodextrin | 20.0% w/w |
| Hydroxypropylmethyl cellulose | 20.0% w/w |
| Water | 60.0% w/w |

Expansion 50 g of homogeneous dispersion were poured (dose: 325 mg dry mass) into the holes of PVC tablet blister packs. After covering with a sieve (mesh size 0.5 mm) the blister packs were put into a vacuum drying oven (Heraeus VT 5050 EK). At ambient temperature chamber pressure was lowered to 75 Torr (Leybold Heraeus TRIVAC D8B; COMAT AG DPI 700). After 15 minutes, expansion of structure was completed.

Drying by measuring mass and chamber temperature (AOiP PJN 5210) the chamber temperature was then increased to 50° C. for about 120 minutes.

the readily dried foam tablets fell easily out of the turned blister pack, showed a smooth surface, good physical stability respectively low friability and a satisfactory uniformity of weight (n=10; mv=323.7 mg; sd=±2.6%).

What is claimed is:

1. A method for preparing a pharmaceutical composition containing orlistat, which comprises:
   a) preparing a solution or a homogeneous dispersion, which contains a liquid, orlistat, and one or more pharmaceutically suitable excipients;
   b) expanding the solution or homogeneous dispersion by exposing it to a reduction in pressure to between about 30 and about 150 Torr under conditions such that the solution or homogeneous dispersion does not boil; and
   c) stabilizing the expanded solution or homogeneous dispersion to form the pharmaceutical composition.

2. The method of claim 1, wherein stabilizing comprises drying or cooling the composition.

3. The method of claim 1, wherein the solution or dispersion comprises an embedding material or glass matrix-forming material.

4. The method of claim 3, wherein the embedding material or glass matrix-forming material is a pharmaceutically suitable excipient.

5. The method of claim 4, wherein the embedding material or glass matrix-forming material is a polyol, gum, polymer, or a pharmaceutically acceptable salt thereof.

6. The method of claim 5, wherein the embedding material or glass matrix-forming material is a polyol that is a carbohydrate.

7. The method of claim 6, wherein the carbohydrate is selected from the group consisting of maltodextrin, trehalose, cellobiose, glucose, fructose, maltulose, isomaltulose, lactulose, maltose, gentobiose, lactose, isomaltose, maltitol, lactitol, erythritol, palatinitol, xylitol, mannitol, sorbitol, dulcitol and ribitol, trehalose, sucrose, raffinose, gentianose, planteose, verbascose, stachyose, melezitose, dextran, and inositol.

8. The method of claim 7, wherein the carbohydrate is maltodextrin.

9. The method of claim 7, wherein the carbohydrate is maltitol.

10. The method of claim 7, wherein the carbohydrate is trehalose.

11. The method of claim 5, wherein the gum, polymer or pharmaceutically acceptable salts thereof is selected form the group consisting of polyethylenglycol; modified or substituted starch; modified or substituted cellulose; povidone; polyvinyl-alcohol; acacia gum; carbomer; alginic acid; cyclodextrins; gelatin; guar gum; welan gum; gellan gum; tara gum; locust bean gum; fibers; carrageenan gum; glucomannan; polymethacrylates; propylene glycol alginate; shellac; sodium alginate; tragacanth; chitosan; and xanthan gum.

12. The method of claim 11, wherein the gum, polymer or pharmaceutically acceptable salts thereof is a modified or substituted starch that is selected from the group consisting of is pregelatinized starch, hydroxyethylstarch, and sodium starchoctenylsucciante.

13. The method of claim 11, wherein the gum, polymer or pharmaceutically acceptable salts thereof is a modified or substituted cellulose that is selected from the group consisting of is methylcellulose, ethylcellulose, hydroxyethyl cellulose, hydroxypropyl cellulose, hydroxypropylmethyl cellulose, hydroxypropylmethyl cellulose phthalate, carboxymethylcellulose sodium, and cellulose acetate phthalate.

14. The method of claim 1, wherein the solution or dispersion comprises a tenside.

15. The method of claim 14, wherein the tenside is selected from the group consisting of anionic tensides, co-emulsifiers, cationic tensides, non-ionic tensides, and amphoteric tensides.

16. The method of claim 15, wherein the tenside is selected from the group consisting of sodium lauryl sulfate, docusate sodium, caseinate sodium, salts of fatty acids, quaternary amines, cethylpyridiniumchloride, polyoxyethylene fatty acid esters, sucrose fatty acid esters, cetyl alcohol, fatty acid esters, cetostearyl alcohol, cholesterol, sorbitan fatty acid esters, polysorbats, poloxamers, tocopheryl polyethylene glycol succinate, and phospholipids.

17. The method of claim 1, wherein the solution or dispersion consists essentially of about 5 to about 95% w/w water or a mixture of water/ethanol, about 1 to about 91% orlistat, about 3.9 to about 93.9% w/w maltodextrin, and about 0.1 to about 90.1% w/w of one or more pharmaceutically acceptable excipients.

18. The method of claim 1, wherein the solution or dispersion consists essentially of about 5 to about 95% w/w water or a mixture of water/ethanol, about 1 to about 91% orlistat, about 3.9 to about 93.9% w/w maltodextrin, and about 0.1 to about 90.1% w/w of polyoxyethylene fatty acid ester.

19. The method of claim 1, wherein the solution or dispersion consists essentially of about 5 to about 95% w/w water or mixtures of water/ethanol, about 1 to about 91% w/w orlistat, about 1 to about 91% w/w trimyristin, about 2.9 to about 92.9% w/w maltodextrin, and about 0.1 to about 90.1% w/w polyoxyethylene fatty acid ester.

20. The method of claim 1, wherein the solution or dispersion consists essentially of about 3 to about 99.98% w/w isopropyl alcohol, about 0.01 to about 96.99% w/w oseltamivir, and about 0.01 to about 96.99% w/w polymethacrylate.

21. The method of claim 1, wherein the pharmaceutical composition has a residual solvent level between about 0.1 and about 10% w/w.

22. The method of claim 1, where in the pharmaceutical composition has a bulk (poured) density between about 0.1 and about 10% w/w.

23. The method of claim 1, wherein the pharmaceutical composition has a particle size distribution between about 50 and about 600 µm.

24. The method claim 1, wherein the composition is in final dosage form.

25. The method of claim 1, wherein the composition is prepared inside of its packaging.

26. A composition which comprises about 0.2 to about 10% w/w residual water or a mixture of water/ethanol, about 1 to about 96% w/w orlistat, about 3.7 to about 98.7% maltodextrin, and about 0.1 to about 95.1% w/w of one or more pharmaceutically acceptable excipients.

27. The compositions of claim 26, wherein the composition has a bulk (poured) density between about 0.1 and about 0.9 g/cm$^3$.

28. The composition of claim 26, wherein the composition has a particle size distribution between about 50 and about 600 µm.

29. The composition according to claims 26, wherein the composition has a residual solvent level between 0.1 and 10%.

* * * * *